United States Patent [19]
Tsutsumi

[11] Patent Number: 5,215,043
[45] Date of Patent: Jun. 1, 1993

[54] STEAM GENERATOR FOR A STEAM BATH

[75] Inventor: Hidemi Tsutsumi, Chuo, Japan

[73] Assignee: Mitsui Mining Company, Ltd., Tokyo, Japan

[21] Appl. No.: 960,233

[22] Filed: Oct. 13, 1992

Related U.S. Application Data

[63] Continuation of Ser. No. 656,943, Feb. 19, 1991, abandoned.

[51] Int. Cl.⁵ ............................................. F22B 27/00
[52] U.S. Cl. .................................... 122/39; 261/108; 261/112.1; 122/40
[58] Field of Search .................. 122/31 R, 39, 40; 261/108, 112.1

[56] References Cited

U.S. PATENT DOCUMENTS

| | | | |
|---|---|---|---|
| 279,848 | 6/1883 | Ward | 261/108 |
| 975,156 | 11/1910 | Pieplu | 261/108 |
| 1,246,704 | 11/1917 | Boeckem | 261/108 |
| 2,645,607 | 7/1953 | Allen | 122/39 |
| 4,133,709 | 1/1979 | Carrico | 261/112.1 |
| 4,149,901 | 4/1979 | Morales | 261/108 |
| 4,156,705 | 5/1979 | Ogawa et al. | 261/112.1 |
| 4,477,396 | 10/1984 | Wilkinson | 261/112.1 |
| 4,530,347 | 7/1985 | Baker et al. | 122/31.1 |

*Primary Examiner*—Henry C. Yuen
*Attorney, Agent, or Firm*—Oliff & Berridge

[57] ABSTRACT

A steam generator for a steam bath for generating steam from hot water supplied thereto. The steam generator for a steam bath has a closed main part equipped with a hot-water supply port, an air inlet, a discharge port and a steam outlet. Hot water received from the hot-water supply port is distributed in the main part so as to contact with air coming through the air inlet, and the thus generated steam is discharged through the steam outlet. Warm water formed as a result of steam generation is discharged from the discharge port.

7 Claims, 7 Drawing Sheets

STEAM GENERATOR FOR A STEAM BATH

This is a continuation of application Ser. No. 07/656,943 filed Feb. 19, 1991, now abandoned.

BACKGROUND OF THE INVENTION

1. Field of the Invention

The present invention relates to a steam generator for a steam bath for generating steam from hot water and, more particularly, to a steam generator for a steam bath which is used for raising temperature and humidity in a closed section such as a bathroom.

2. Description of the Related Art

It is known to generate steam in a closed section such as a bath room for the purpose of raising the air temperature or for the purpose of creating the condition of a sauna.

Steam for such purposes may be of a comparatively low temperature below 100° C., so that it is desirable that the steam is generated easily by a simple device.

A small-scale boiler therefore has been used for such purposes. The boiler, however, requires various safety devices and control system because it has a heat source and a boiling chamber.

Thus, the known steam generating system using a boiler is not suitable for household use because of the necessity for laborious maintenance and administration work and because of a high cost.

SUMMARY OF THE INVENTION

Accordingly, an object of the present invention is to provide a steam generator for a steam bath which is easy to install in, for example, a bath room and to maintain and administer, and which can easily generate steam.

To this end, according to the present invention, there is provided a steam generator for a steam bath for generating steam from hot water supplied thereto, comprising: a closed main part equipped with a hot-water supply port, an air inlet, a discharge port and a steam outlet; and means for distributing the hot-water in the main part so as to make the hot water contact with air coming through the air inlet, thereby generating steam and and discharging the generated steam through the steam outlet.

These and other objects, features and advantages of the invention will become clear from the following description of the preferred embodiments when the same is read in conjunction with the accompanying drawings.

DESCRIPTION OF THE PREFERRED EMBODIMENTS

Figure 1:
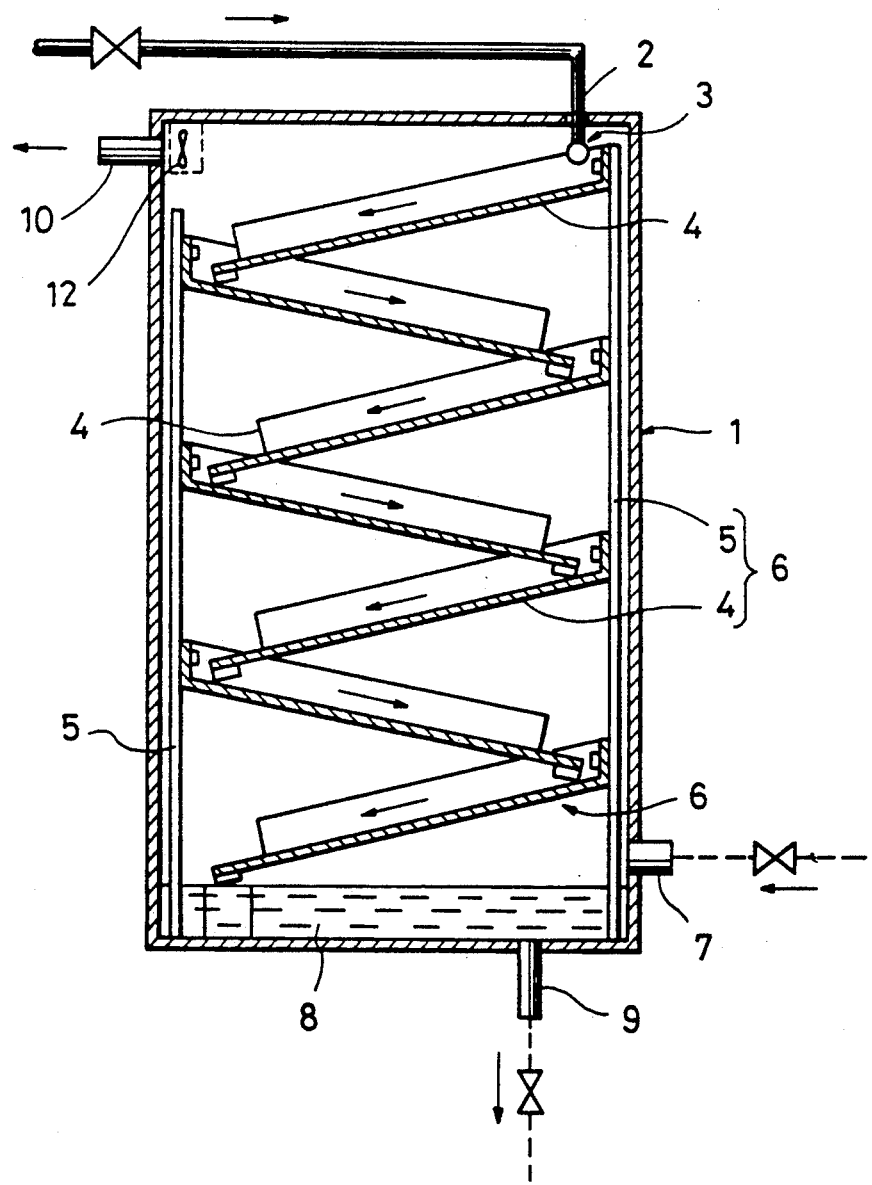
FIG. 1 is a schematic sectional view of a first embodiment of the steam generator for a steam bath in accordance with the present invention.

Referring to FIG. 1 showing a first embodiment of the steam generator for a steam bath in accordance with the present invention, the steam generator for a steam bath has a hot-water supply port 2 provided on a top portion of a main part 1 of the steam generator for a steam bath, a hot-water distribution header 3 connected to the hot-water supply port 2 and for distributing and scattering hot water, a plurality of slant flow plates 4,4 which are arranged to receive the hot water distributed by the hot-water distribution header 3 and for guiding downward flow of the hot water in a zig-zag manner towards the lower end of the main body 1, four legs 5 which fix the slant flow plates 4,4 in the main part 1, the slant flow plates 4,4 and the legs 5 in combination forming a flow-down structure 6, an air inlet 7 provided in the lower end of the side wall of the main part 1, a warm water reservoir 8 for storing the warm water discharged from the lowermost slant flow plate 4, a discharge port 9 through which the warm water is discharged from the warm water reservoir 8, a steam outlet 10 provided in an upper part of the main part 1 so as to allow the steam, which is generated in the steam generator for a steam bath and ascends together with ascending air flow, to be discharged to the exterior of the steam generator for a steam bath and a fan 12 provided on the top of the main part 1 at a position in the vicinity of the steam outlet 10.

Figure 2:
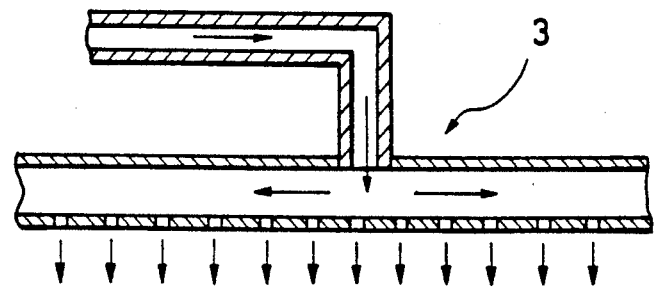
FIG. 2 is a schematic illustration of a hot-water distribution header.

As shown in FIG. 2, the hot-water distribution header 3 is provided with a plurality of holes so that hot water is uniformly distributed and sprayed therefrom.

Various forms of the slant flow pate 4 are shown in FIGS. 3(a) to 3(e). In general, the slant flow plate 4 has a bottom wall 13, side walls 14 protruding from three sides, i.e., the top and both lateral sides, of the bottom wall 13, and depending portions 15 depending from the remaining side, i.e., the lower side, of the bottom wall 13. The side walls 14 are cut-away at portions near the depending portions 15.

These slant flow plates 14 are arranged from the top end to the bottom end of the main part 1 with an alternating slanting directions, i.e., in a zig-zag manner, with their top edges fastened to the legs 5 while the depending portions 15 resting on the bottom wall 13 of the downstream underlying slant flow plate 4, whereby the successive slant flow plates are held at a predetermined spacing.

By selecting the spacing between both lateral side walls 14 greater than the spacing between both depending portions 15 in each slant flow plate 14, it is possible to securely hold the overlying upstream slant flow plate 4 by the subsequent downstream slant flow plate 4.

The bottom wall 13 of the slant flow plate 4 can have various forms as shown in FIGS. 3(a) to 3(e).

Figures 3A, 3B:
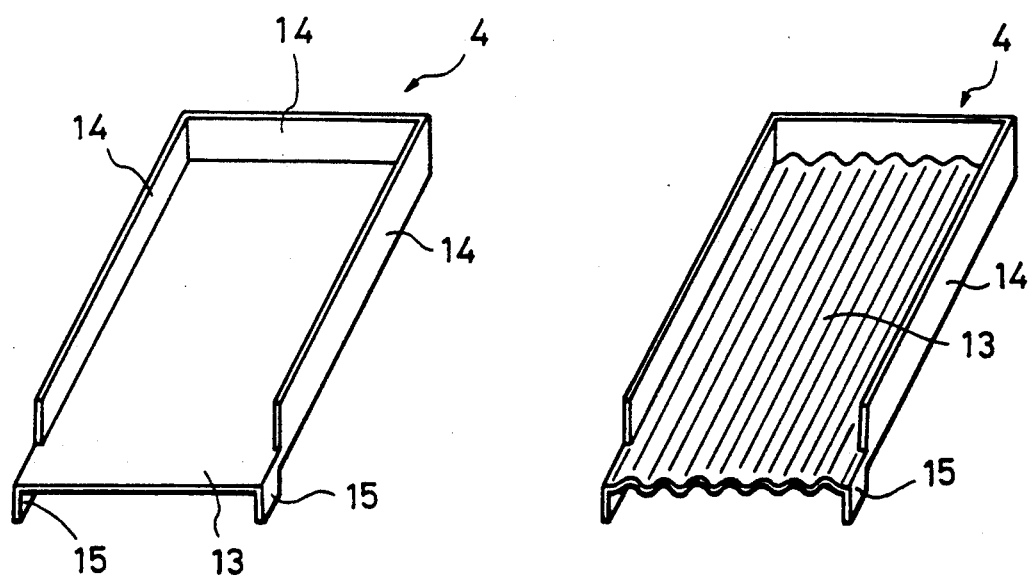
FIGS. 3(a) to 3(e) are illustrations of modifications of slant flow plate used in the embodiments shown in FIG. 1.
Figure 3C:
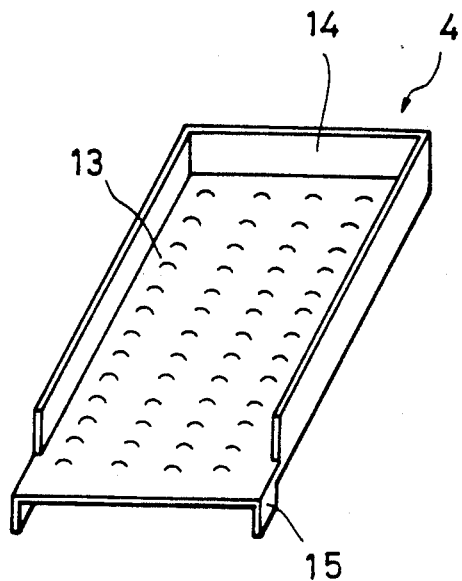
Figure 3D:
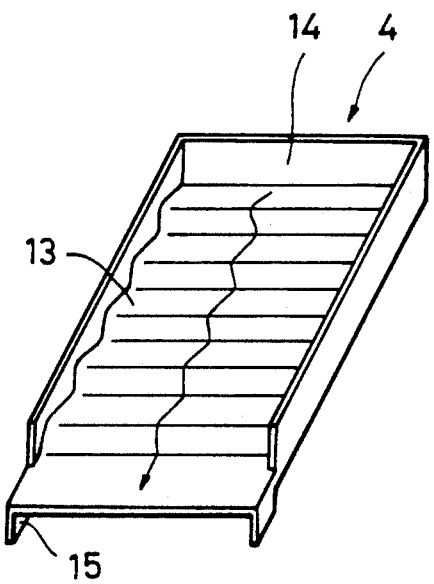
Figure 3E:
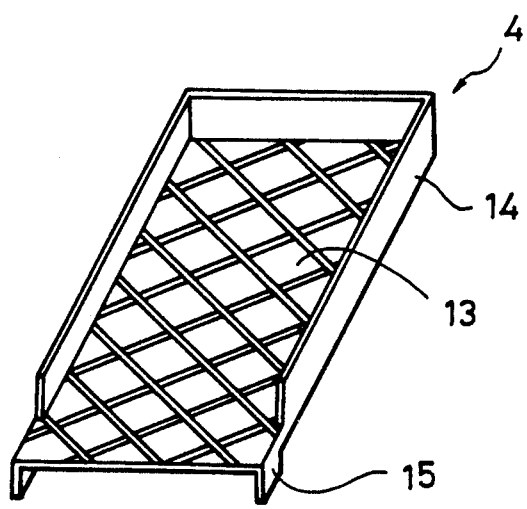

In FIG. 3(a), the slant flow plate has a flat surface, while in FIG. 3(b), the bottom wall 13 has a corrugated surface. The slant flow plate 4 shown in FIG. 3(c) has a multiplicity of projections. In FIGS. 13(d) and 13(e), the bottom walls 13 of the slant flow plates have, respectively, consecutive ridges forming dams and grooves.

The slant flow plate 4 is so sized that a steam ascending passage is formed between the peripheral sides of the vertical stack of the slant flow plates 4 and the opposing walls of the main part 1.

In the described embodiments, the fan 12 is provided on the upper end of the main part 1 in order to facilitate discharge from the steam outlet 10 of the mixture of the steam and air which is induced from the air inlet 7. This fan 12, however, is not essential.

Although the air inlet 7 and the steam outlet 10 have cylindrical forms, this is only illustrative and rectangular cross-sectional shape can be adopted equally well.

A test was conducted using this embodiment employing slant flow plates 4 of 400 mm wide and 500 mm long. In the test, hot water of 73.9° C. was supplied from the hot-water supply port 2 at a rate of 4.5 l/min. Steam generated in the steam generator was discharged through the steam outlet 10 with the assist of the fan 12 into a closed room having an internal volume of 3.5 m³.

Before the operation of the steam generator, the air temperature was 20° C. both inside and outside the room. As a result of the operation of the steam generator, the temperature in the room was elevated to 45° C. in 17.7 minutes.

Subsequently, hot water was intermittently supplied at a rate controlled in accordance with the room temperature. As a result, a steam sauna atmosphere of 45° C. and 100% humidity could be maintained in the room.

Figure 4:
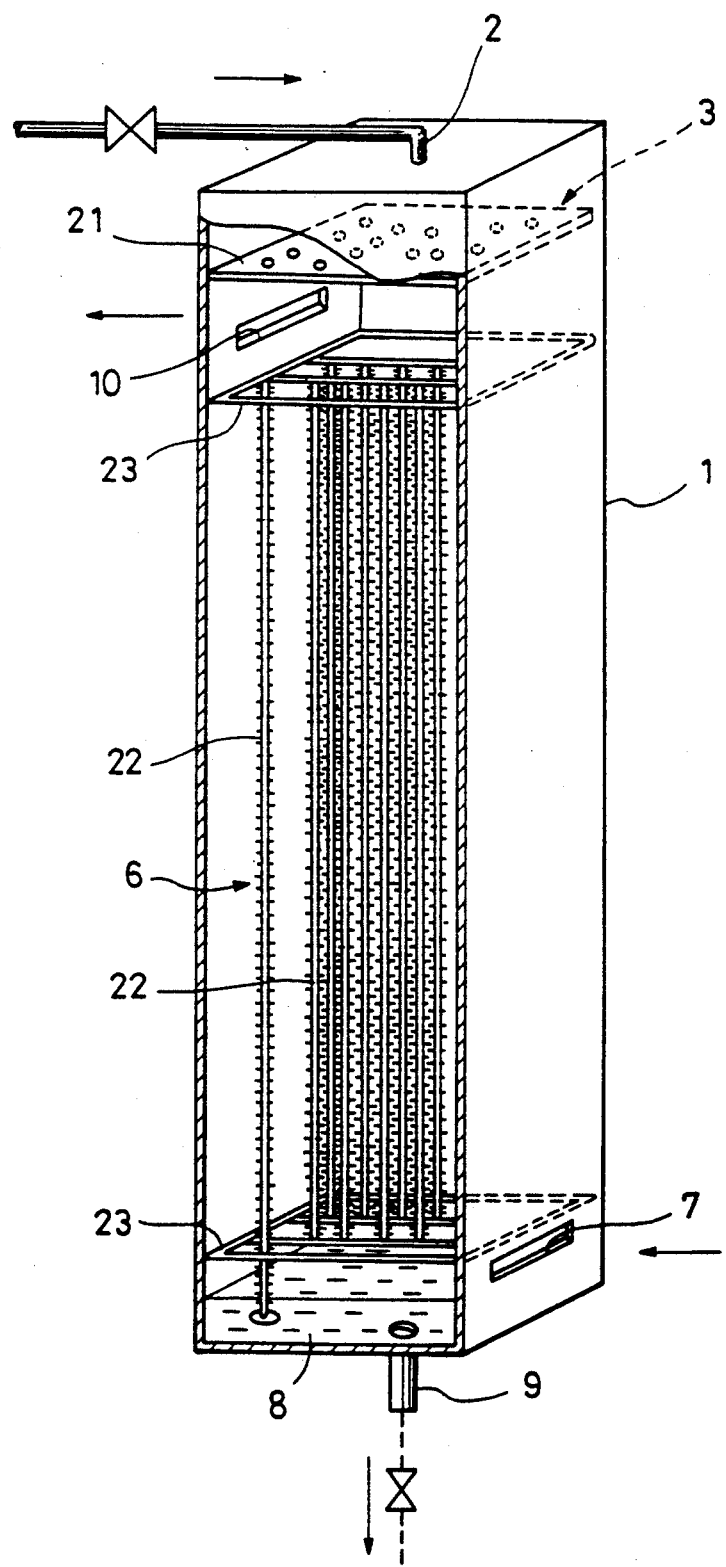
FIG. 4 is a schematic sectional view of another embodiment of the steam generator for a steam bath of the present invention.

FIG. 4 shows a second embodiment of the steam generator of the present invention.

This embodiment has a hot-water supply port 2 provided, on a top portion of a main part 1 of the steam generator for a steam bath, a hot-water distribution header 3 including a perforated distribution plate 21 provided on the upper portion of the main part 1 for distributing and scattering hot water supplied from the hot-water supply port 2, a plurality of finned tubes 22 provided under the hot-water distribution head 3, the finned tubes 22 having closed upper ends and extended vertically between upper and lower frames 23 provided in upper and lower portions of the main part 1, the finned tubes 22 presenting a flow-down structure 6, an air inlet 7 provided in the lower end of the side wall of the main part 1, a warm water reservoir 8 disposed in a lower portion of the main part 1 and adapted for storing the warm water, a discharge port 9 through which the warm water is discharged from the warm water reservoir 8, a steam outlet 10 provided in an upper portion of the main part 1 immediately below the distribution plate 21 so as to allow the steam, which is generated in the steam generator for a steam bath and ascends together with ascending air flow, to be discharged to the exterior of the steam generator for a steam bath, and a fan (not shown) for forcibly discharging the steam-air mixture to the exterior of the steam generator for a steam bath.

The finned tubes 22 on four corners have a length which is large enough to enable these finned tubes 22 to contact the bottom of the main part 1, thus stabilizing the flowdown structure 6.

A test was conducted using this embodiment employing the flow-down structure 6 having 24 finned tubes 22 (total area 1.5 m²) arranged in six rows and 4 columns, each finned tube having a tube diameter of 10 mm, fin diameter of 16 mm, fin pitch of 25 mm and a tube length of 1 m. In the test, hot water of 73.9° C. was supplied from the hot-water supply port 2 at a rate of 4.8 l/min.

A mixture (about 50° C.) of steam generated in the steam generator for a steam bath and air was discharged through the steam outlet 10 with the assist of the fan into a closed room having an internal volume of 3.5 m³.

Before the operation of the steam generator for a steam bath, the air temperature was 22.5° C. both inside and outside the room. As a result of the operation of the steam generator for a steam bath, the temperature in the room was elevated to 45° C. in 10.8 minutes.

Subsequently, hot water was intermittently supplied at a rate controlled in accordance with the room temperature. As a result, a steam sauna atmosphere of 45° C. and 100% humidity could be maintained in the room.

Figure 5:
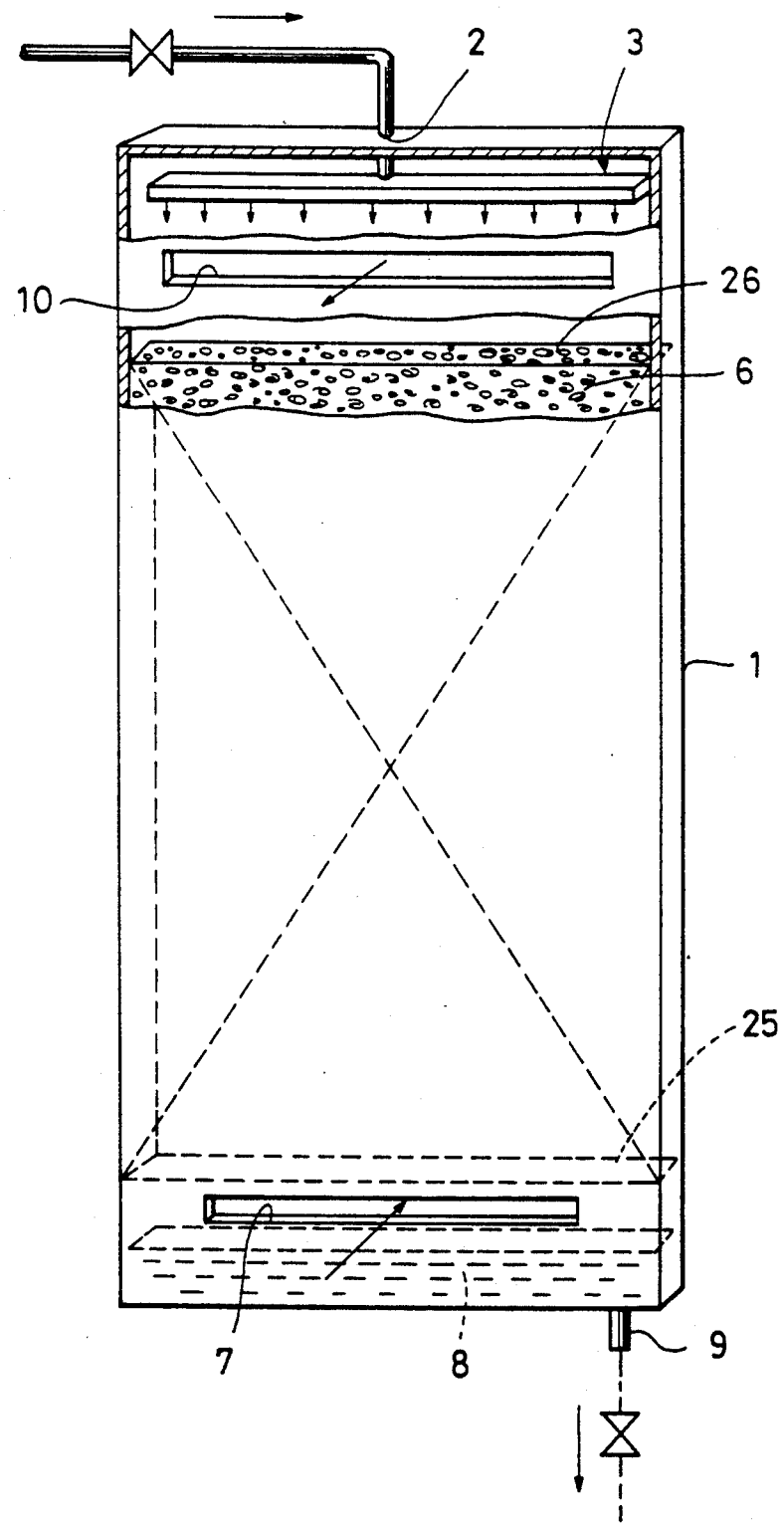
FIG. 5 is a schematic sectional view of a third embodiments of the steam generator for a steam bath of the present invention.

FIG. 5 shows a third embodiment of the steam generator for a steam bath of the present invention.

This embodiment has a hot-water supply port 2 provided on a top portion of a main part 1 of the steam generator for a steam bath, a hot-water distribution header 3 disposed on upper end portion of the main part 1 in communication with the hot-water supply port 2 and having a plurality of holes for distributing and spraying hot water, a filler assembly 26 supported by a supporting net 25 provided on the lower end portion of the main part 1, the filler assembly 26 presenting a flow-down structure 6, an air inlet 7 provided in a lower portion of the side wall of the main part 1 below the supporting network 25, a warm water reservoir 8 for storing the warm water flowing down through the flow-down structure 6, a discharge port 9 through which the warm water is discharged from the warm water reservoir 8, a steam outlet 10 provided in an upper portion of the main part 1 so as to allow a mixture of the steam which is generated in the steam generator for a steam bath and air induced through the air inlet 7 to be discharged to the exterior of the main part 1, and a fan (not shown) for forcibly discharging the steam-air mixture to the exterior of the steam generator for a steam bath.

The filler assembly 26 was composed of a three-dimensional network structure of 600 mm wide, 35 mm thick and 1.1 m high, formed by stacking a multiplicity of coiled plastic wire having a wire diameter of 2 mm.

The filler assembly 26 should be stable against any deformation caused by the heat of the hot water. Various types of materials such as a linear three-dimensional network structure and other structures such as granular, bulbous, labyrinth, saddle-shaped and paling type structures can be used.

In the illustrated embodiments, the air inlet 7 and the steam outlet 10 are formed in the same side wall. This, however, is only illustrative and the air inlet 7 and the steam outlet 10 may be provided in opposing side walls of the filler assembly 26.

A test was conducted using this embodiment. In the test, hot water of 73.9° C. was supplied from the hot-water supply port 2 at a rate of 4.7 l/min. A mixture (about 50° C.) of steam generated in the steam generator for a steam bath and air was discharged through the steam outlet 10 with the assist of the fan into a closed room having an internal volume of 3.5 m³.

Before the operation of the steam generator, the air temperature was 19° C. both inside and outside the room. As a result of the operation of the steam generator, the temperature in the room was elevated to 45° C. in 8.5 minutes.

Subsequently, hot water was intermittently supplied at a rate controlled in accordance with the room temperature. As a result, a steam sauna atmosphere of 45° C. and 100% humidity could be maintained in the room.

Figure 6:
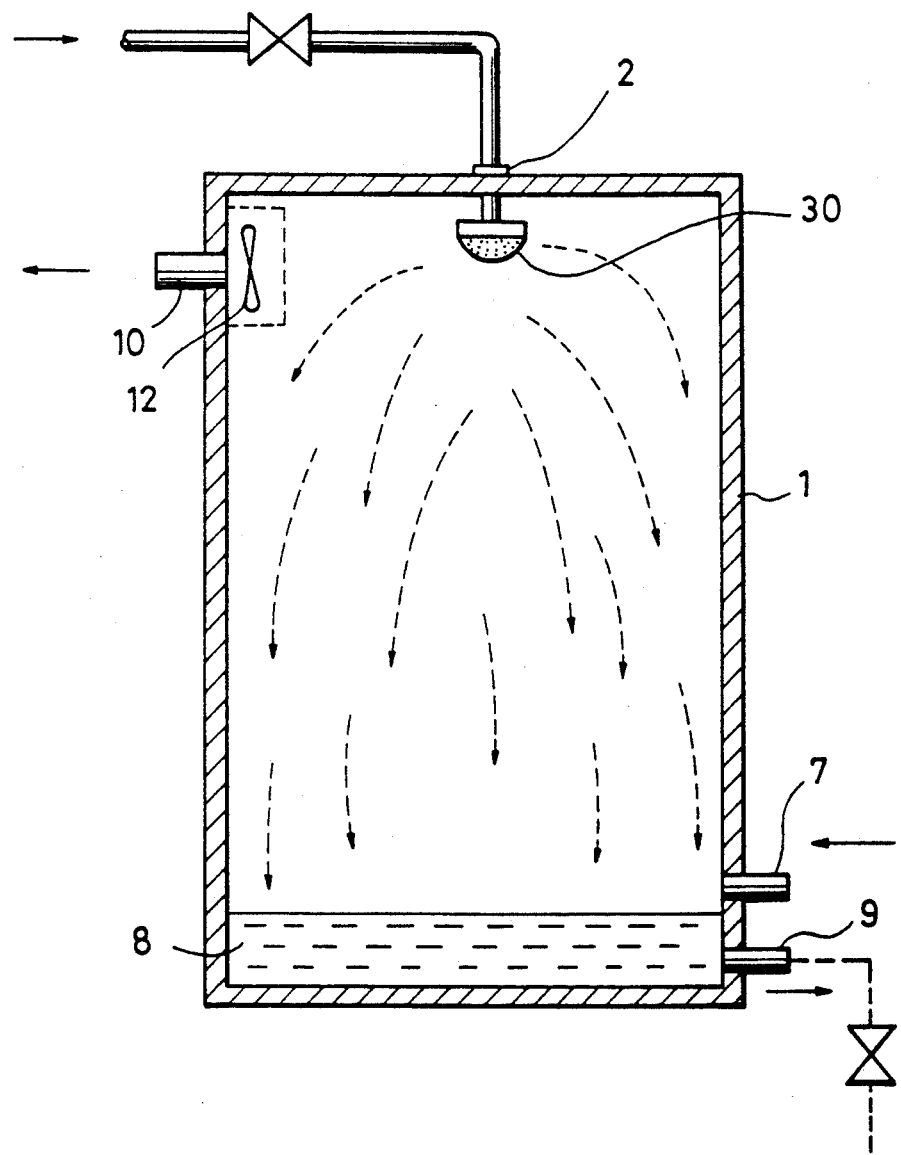
FIG. 6 is a schematic sectional view of a fourth embodiments of the steam generator for a steam bath of the present invention.

FIG. 6 shows a fourth embodiment of the steam generator for a steam bath of the present invention.

This embodiment has a hot-water supply port 2 provided on a top portion of a cylindrical main part 1 of the steam generator for a steam bath, a hot-water spray nozzle 30 connected to the hot-water supply port 2 and adapted for distributing or spraying the hot water, an air inlet 7 provided in a lower portion of the side wall of the main part 1, a warm water reservoir 8 for storing the warm water which is generated as a result of generation of steam from the hot-water sprayed from the hot-water spray nozzle 30 and flowing down along the side walls of the main part 1 and the space inside the main part 1, a discharge port 9 through which the warm water is discharged from the warm water reservoir 8, a steam outlet 10 provided in an upper portion of the side wall of the main part 1 so as to allow a mixture of the steam which is generated in the steam generator for a steam bath and air induced through the air inlet 7 to be discharged to the exterior of the main part 1, and a fan 12 disposed on an upper portion of the main part 1 near the steam outlet 10 and adapted for forcibly discharging the steam-air mixture to the exterior of the main part 1.

In the illustrated embodiment, the main part 1 is sized to have a diameter of 250 mm and a height of 1900 mm.

A test was conducted using this embodiment. In the test, hot water of 73.9° C. was supplied from the hot-water supply port 2 at a rate of 2.3 l/min from the hot-water spray nozzle 30 provided in the top portion of the main part 1. Ascending mixture (about 50° C.) of steam generated in the steam generator for a steam bath and air was discharged through the steam outlet 10 with the assist of the fan 12 into a closed room having an internal volume of 3.5 m$^3$.

Before the operation of the steam generator for a steam bath, the air temperature was 20° C. both inside and outside the room. As result of the operation of the steam generator for a steam bath, the temperature in the room was elevated to 45° C. in 8.5 minutes.

Subsequently, hot water was intermittently supplied at a rate controlled in accordance with the room temperature. As a result, a steam sauna atmosphere of 45° C. and 100% humidity could be maintained in the room.

Although the air inlet 7 and the steam outlet 10 have cylindrical forms in the illustrated embodiments, this is only illustrative and rectangular forms may be adopted equally well.

Figure 7:
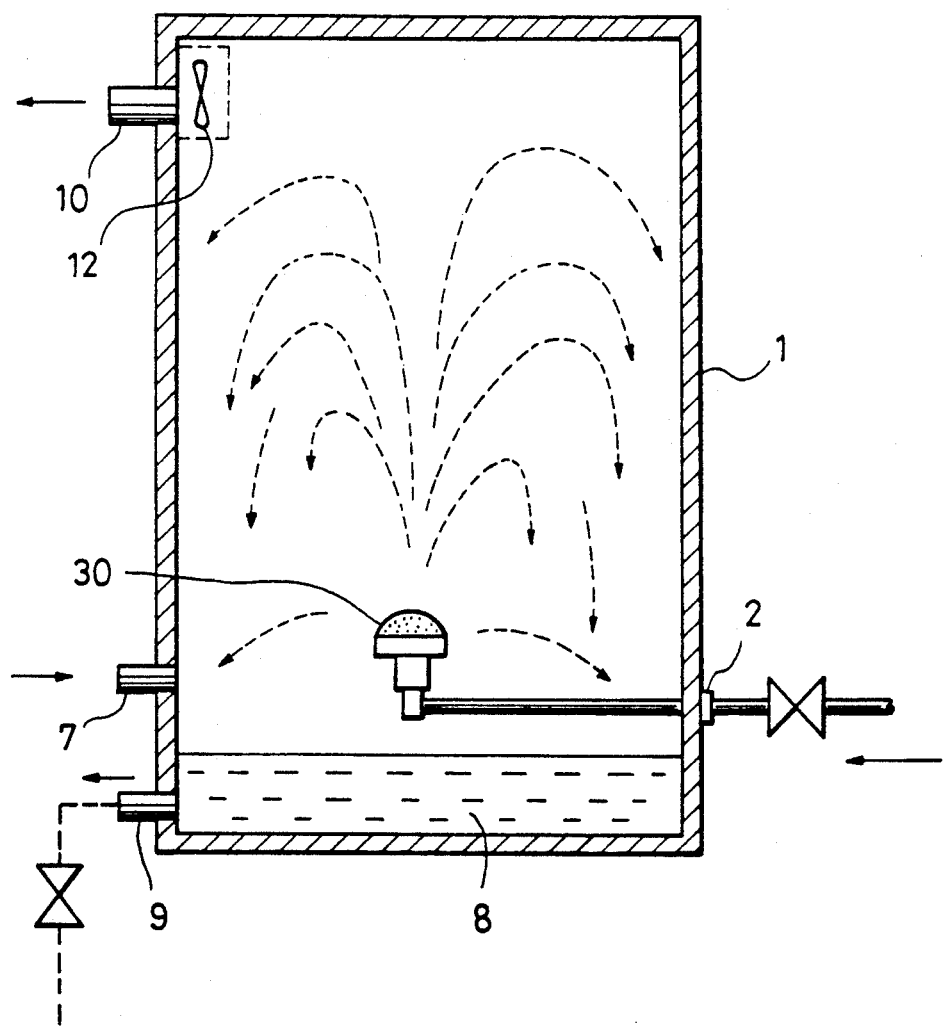
FIG. 7 is a schematic sectional view of a fifth embodiments of the steam generator for a steam bath of the present invention.

FIG. 7 shows a fifth embodiment of the steam generator for a steam bath of the present invention.

This embodiment has a hot-water supply port 2 provided in a lower portion of the side wall of a cylindrical main part 1 of the steam generator for a steam bath, a hot-water spray nozzle 30 which is disposed at a central portion of the space inside the main part 1 and which is connected to the hot-water supply port 2 so as to distribute or spray the hot water, an air inlet 7 provided in a lower portion of the side wall of the main part 1, a warm water reservoir 8 formed by the bottom portion of the main part 1 below the hot-water spry nozzle 30 and adapted for storing the warm water which is generated as a result of generation of steam from the hot-water sprayed from the hot-water spray nozzle 30 and flowing down along the side walls of the main part 1 and the space inside the main part 1, a discharge port 9 which is provided in a lower end portion of the wall of the main part 1 and through which the warm water is discharged from the warm water reservoir 8, a steam outlet 10 provided in an upper portion of the side wall of the main part 1 so as to allow a mixture of the steam which is generated in the steam generator for a steam bath and air induced through the air inlet 7 to be discharged to the exterior of the main part 1, and a fan 12 disposed on an upper portion of the main part 1 near the steam outlet 10 and adapted for for forcibly discharging the steam-air mixture to the exterior of the main part 1.

In the illustrated embodiments, the main part 1 is sized to have a diameter of 250 mm and a height of 1900 mm.

A test was conducted using this embodiment. In the test, hot water of 73.9° C. was supplied from the hot-water supply port 2 at a rate of 2.3 l/min from the hot-water spray nozzle 30 provided in the lower portion of the main part 1. Ascending mixture (about 50° C.) of steam generated in the steam generator for a steam bath and air was discharged through the steam outlet 10 with the assist of the fan 12 into a closed room having an internal volume of 3.5 m$^3$.

Before the operation of the steam generator for a steam bath, the air temperature was 20° C. both inside and outside the room. As a result of the operation of the steam generator for a steam bath, the temperature in the room was elevated to 45° C. in 12 minutes.

Subsequently, hot water was intermittently supplied at a rate controlled in accordance with the room temperature. As a result, a steam sauna atmosphere of 45° C. and 100% humidity could be maintained in the room.

Although the air inlet 7 and the steam outlet 10 have cylindrical forms in the illustrated embodiments, this is only illustrative and rectangular forms may be adopted equally well.

As will be understood from the foregoing description, the steam generator for a steam bath of the present invention can generate steam by making an efficient use of hot water of a comparatively low temperature below 100° C., without requiring anti-overheat or other safety devices which are required in conventional steam generators employing boilers, thus facilitating installation and operation and improving safety.

What is claimed is:

1. A steam generator for a steam bath, comprising:
   a closed main part having a support structure, a hot-water supply port, an air inlet, a warm-water discharge port and a steam outlet, said steam outlet opening into a room comprising the steam bath to create a sauna atmosphere therein;
   a hot-water distributing member provided in said main part for receiving hot water from said hot-water supply port and distributing the received hot water;
   a flow-down structure disposed in said main part, wherein said flow-down structure includes a plurality of flow plates one above another in alternating slanting directions, with top edges of said flow plates fastened to said support structure while depending portions of said flow plates rest upon a bottom wall of a downstream underlying flow plate such that bottom walls of successive flow plates are held at a predetermined spacing by at least one flow plate depending portion of an upstream overlying flow plate, and the distributed hot-water flows down along said flow-down structure, said flow-down structure having a large surface area, such that steam is generated from the hot water flowing down along said flow-down structure and the generated steam is discharged from said steam outlet together with air introduced from said air inlet, and a warm water reservoir to collect discharge from a lowermost portion of said flow-down structure.

2. The steam generator for a steam bath according to claim 1, wherein a fan is disposed in said main part at a position near said steam outlet.

3. The steam generator for a steam sauna bath according to claim 2, wherein each of said flow plates includes said bottom wall having a surface which has projections and recesses and along which hot water flows.

4. An apparatus for generating steam from hot water, comprising:

a main housing having a support structure therein;

a hot water supply means for supplying hot water to the main housing;

an air supply means for supplying air to the main housing;

a warm water discharge means for discharging warm water from the main housing;

a steam generating means disposed within the main housing comprising a plurality of slanted flow plates vertically arranged in alternating directions, with top edges of said flow plates fastened to said support structure while depending portions of said flow plates rest upon a bottom wall of a downstream underlying flow plate such that the bottom walls of successive flow plates are held at a predetermined spacing by at least one flow plate depending portion for combining the hot water and the air to generate steam;

a distribution means disposed within the main housing for distributing the hot water about the steam generating means;

a steam discharge means comprising a fan disposed at a top portion of said main housing for discharging steam from the main housing to a room comprising the apparatus to create a sauna atmosphere therein; and a warm water reservoir for collecting warm water discharge at a lowermost portion of said steam generating means.

5. The apparatus of claim 4, wherein each of the plurality of flow plates comprises said bottom wall having a flow surface which has a plurality of projections and recesses formed on the flow surface and along which hot water flows.

6. The apparatus of claim 4, wherein a temperature of the air supplied by the air supply means is always lower than a temperature of the hot water supplied by the hot water supply means.

7. The apparatus of claim 4, wherein a temperature of the hot water supplied by the hot water supply means is between 60° C. and 80° C.

* * * * *